(12) United States Patent
Angelini et al.

(10) Patent No.: US 11,879,119 B2
(45) Date of Patent: Jan. 23, 2024

(54) PERFUSION BIOREACTOR DRIVEN BY OSMOTIC PRESSURE GRADIENTS

(71) Applicant: University of Florida Research Foundation, Inc., Gainesville, FL (US)

(72) Inventors: Thomas Ettor Angelini, Gainesville, FL (US); Tapomoy Bhattacharjee, Gainesville, FL (US); Wallace Gregory Sawyer, Gainesville, FL (US); Cameron Morley, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 384 days.

(21) Appl. No.: 17/263,712

(22) PCT Filed: Aug. 1, 2019

(86) PCT No.: PCT/US2019/044677
§ 371 (c)(1),
(2) Date: Jan. 27, 2021

(87) PCT Pub. No.: WO2020/028672
PCT Pub. Date: Feb. 6, 2020

(65) Prior Publication Data
US 2021/0163867 A1 Jun. 3, 2021

Related U.S. Application Data (60) Provisional application No. 62/713,215, filed on Aug. 1, 2018.

(51) Int. Cl.
*C12M 1/12* (2006.01)
*C12M 1/26* (2006.01)
(Continued)

(52) U.S. Cl.
CPC ........... *C12M 25/04* (2013.01); *A01N 1/0231* (2013.01); *C12M 1/20* (2013.01); *C12M 23/12* (2013.01);
(Continued)

(58) Field of Classification Search
CPC ........ C12M 25/04; C12M 1/20; C12M 23/12; C12M 23/34; C12M 25/16; C12M 29/04;
(Continued)

(56) References Cited

U.S. PATENT DOCUMENTS

| | | | |
|---|---|---|---|
| 2,340,110 | A | 1/1944 | D'Alelio |
| 2,340,111 | A | 1/1944 | D'Alelio |

(Continued)

FOREIGN PATENT DOCUMENTS

| | | | |
|---|---|---|---|
| WO | 199739624 | A1 | 10/1997 |
| WO | 2016182969 | A1 | 11/2016 |

OTHER PUBLICATIONS

Li, Ceramic Membranes for Separation and Reaction, p. 14-16.
(Continued)

*Primary Examiner* — Samuel P Siefke
*Assistant Examiner* — Henry H Nguyen
(74) *Attorney, Agent, or Firm* — Thomas | Horstemeyer, LLP (57) ABSTRACT

Disclosed herein is a bioreactor system that allows perfusive flow through a porous support medium enabling 3D growth of biological samples. In some embodiments, the system comprises a sample well filled with a three-dimensional (3D) cell growth medium. The system can further comprises a liquid medium reservoir fluidly connected to the sample well by a first filter material. The system can further comprises a medium collection chamber fluidly connected to the sample well by a second filter material. The system can further comprise an absorbant material that creates an
(Continued)

osmotic pressure gradient to produce perfusive flow. In some embodiments, osmotic pressure draws fluid from the liquid medium reservoir, through the first filter material, into the sample well where it permeates the three-dimensional cell growth medium, through the second filter material, and finally into the medium collection chamber.

8 Claims, 10 Drawing Sheets

(51) Int. Cl.
    *C12M 1/00*     (2006.01)
    *C12M 1/32*     (2006.01)
    *C12M 1/20*     (2006.01)
    *A01N 1/02*     (2006.01)
    *C12N 5/00*     (2006.01)

(52) U.S. Cl.
    CPC ............ *C12M 23/34* (2013.01); *C12M 25/16* (2013.01); *C12M 29/04* (2013.01); *C12M 33/00* (2013.01); *C12N 5/0018* (2013.01); *C12N 5/0062* (2013.01)

(58) Field of Classification Search
    CPC .... C12M 33/00; A01N 1/0231; C12N 5/0018; C12N 5/0062
    See application file for complete search history.

(56) References Cited

U.S. PATENT DOCUMENTS

| | | | |
|---|---|---|---|
| 2,533,635 | A | 12/1950 | Seymour |
| 3,940,351 | A | 2/1976 | Schlatzer, Jr. |
| 4,062,817 | A | 12/1977 | Westerman |
| 5,034,486 | A | 7/1991 | Tzai et al. |
| 5,034,487 | A | 7/1991 | Tzai et al. |
| 5,034,488 | A | 7/1991 | Tzai et al. |
| 5,349,030 | A | 9/1994 | Long, II et al. |
| 2002/0189374 | A1* | 12/2002 | DeSilets ................ C12M 23/12 73/864.51 |
| 2005/0260175 | A1* | 11/2005 | Hedrick ................ C12M 47/04 435/366 |
| 2008/0176209 | A1* | 7/2008 | Muller ................ B01L 3/5085 435/235.1 |
| 2016/0296927 | A1* | 10/2016 | Kirschhoffer .......... B01L 3/502 |
| 2017/0335267 | A1 | 11/2017 | Janas |

OTHER PUBLICATIONS

International Search Report issued for PCT/US2019/044677, dated Oct. 8, 2019.

Laternser et al., A Novel Microplate 3D Bioprinting Platform for the Engineering of Muscle and Tendon Tissues. SLAS Technology, vol. 23, No. 6, p. 599-613, 2018.

* cited by examiner

PERFUSION BIOREACTOR DRIVEN BY OSMOTIC PRESSURE GRADIENTS

CROSS-REFERENCE TO RELATED APPLICATIONS

This application is a National Stage of International Application No. PCT/US2019/044677, filed Aug. 1, 2019, which claims benefit of U.S. Provisional Application No. 62/713,215, filed Aug. 1, 2018, which is hereby incorporated herein by reference in its entirety.

STATEMENT REGARDING FEDERALLY SPONSORED RESEARCH OR DEVELOPMENT

This invention was made with Government Support under Grant No. DMR1352043 awarded by the National Science Foundation. The Government has certain rights in the invention.

BACKGROUND

The printing or placement of biological samples (e.g., cells, cell layers, tissues) into a 3D support medium more accurately and reproducibly models cellular morphology, heterogeneity, and genetic profiles seen in vivo compared to conventional 2D culture. Some existing 3D cell culture techniques rely on polymer scaffolds in which cells are seeded and allowed to adhere. Once the cells are adhered to the scaffold, perfusion of growth media can begin. This method has several disadvantages: (1) cell migration is limited or precluded, (2) cell environments are defined by the structure of the polymer scaffold, (3) the experimental setup is not time-effective, and (4) does not include optical access for microscopy. In addition, cell viability for existing 3D culture methods is generally limited to several days; the passive 3D support medium cannot efficiently expel cellular waste, leading to localized cytotoxic environments and subsequent cell death.

SUMMARY

Disclosed herein is a bioreactor system that allows perfusive flow through a porous support medium enabling 3D growth of biological samples. In some embodiments, the system comprises a sample well filled with a three-dimensional (3D) cell growth medium. The system can further comprise a medium collection chamber fluidly connected to the sample well by a second filter material. In some embodiments, an absorbant material in the collection chamber creates an osmotic pressure gradient that draws fluid from the sample well of the well plate where it permeates the 3D cell growth medium, through the filter material, and finally into the absorbant material of the collection chamber. Flow rates between 1 microliter per hour and 100 microliters per hour can be sustained over periods between one hour and one day. Perfusion has been demonstrated to significantly increase cell viability.

The details of one or more embodiments of the invention are set forth in the accompanying drawings and the description below. Other features, objects, and advantages of the invention will be apparent from the description and drawings, and from the claims.

DETAILED DESCRIPTION

To combat stagnant toxic environment in 3D culture, a perfusive flow can be induced through the support medium, thereby flowing in nutrient solution and flowing out waste products. The disclosed system vastly improves upon the current standard by introducing a specialized jammed microgel system that allows for cellular migration and perfusion and is experiment ready as soon as the cells are placed within it. The device that houses this gel includes a filter and an osmotic gradient which allows the nutrient media to perfuse through the system without disturbing the cellular environment. In some cases, this system allows for continuous optical access during the growth of the biological samples.

Disclosed herein is a bioreactor system that can involve a multi-well, or continuous-well, platform with optional integrated optical pathways for direct observation of biological samples in bioreactor units. Perfusive flow is used through a porous support medium in the bioreactor enabling 3D growth of biological samples. Optical pathways enable microscopy of biological samples without interruption of perfusion, and allows long-term growth and behavior to be studied without disturbing the environment.

Filter Material

The disclosed bioreactor systems comprise one or more filters that allows the liquid media to perfuse through the system without disturbing the cellular environment.

The filter material can be any combination of biocompatible, or inert, materials which can form a solid and retain a porosity equal to or smaller than the size of the 3D support matrix polymer. Prime examples include Poly(2-hydroxyethyl methacrylate) (pHEMA) polymerized to a degree to which spinodal decomposition occurs, producing a porosity on the order of the 3D support matrix polymer; sintered microparticles including Polyether ether ketone (PEEK), borosilicate, steel, or various ceramics.

The filter material may be composed of nanoporous sheet membranes of material polycarbonate, nylon, or various other materials which produce the same effect while remaining biocompatible or inert.

Osmotic Gradient

As disclosed herein, perfusive flow can be created in the disclosed systems using an osmotic gradient. An osmotic gradient can be generated, for example, by placing an absorbant material in the collection chamber. Swelling of the absorbant material creates a perfusive flow in the system with a flow rate dependent upon the swelling rate.

In some embodiments, a hydrogel polymer is used to generate the osmotic gradient. A charged polymeric network forms a hydrogel in water due to the difference in the osmotic pressure between the network and the surrounding solvent. For example, poly(acrylic acid)-based hydrogels can swell up to 100-1000 times their own weight in desalinated water. Such hydrogels are called superabsorbent materials and are employed in large quantities in sanitary products like diapers.

Therefore, in preferred embodiments, the polymer is a superabsorbent polymer. Examples of superabsorbent material polymers include without limitation the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention.

The superabsorbent polymers can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Pre-formed particulate superabsorbents are generally available in particle sizes ranging from about 20 to about 1000 microns. Examples of suitable commercially available particulate superabsorbents include HYDRASORB® P7050, available from BASF Corporation located in Portsmouth, Va., DRYTECH® 2035 available from Dow Chemical Co. located in Midland, Mich., and FAVOR® SXM 880, available from Stockhausen, Inc. located in Greensborough, N.C. An example of a fibrous superabsorbent is OASIS® 101, available from Technical Absorbents, located in Grimsby, United Kingdom.

In some embodiments, the superabsorbent material is a 3D microgel medium, such as one disclosed below, that is added to the collection chamber while it is still unswelled.

3D Medium

Liquid-like solid (LLS) three-dimensional (3D) cell growth medium for use in with the disclosed bioreactor system is disclosed in WO2016182969A1 by Sawyer et al., which is incorporated by reference in its entirety for the description of how to make and uses this LLS medium.

Briefly, the 3D cell growth medium may comprise hydrogel particles dispersed in a liquid cell growth medium. Any suitable liquid cell growth medium may be used; a particular liquid cell growth medium may be chosen depending on the types of cells which are to be placed within the 3D cell growth medium. For example, suitable cell growth medium may be human cell growth medium, murine cell growth medium, bovine cell growth medium or any other suitable cell growth medium. Depending on the particular embodiment, hydrogel particles and liquid cell growth medium may be combined in any suitable combination. For example, in some embodiments, a 3D cell growth medium comprises approximately 0.5% to 1% hydrogel particles by weight.

In accordance with some embodiments, the hydrogel particles may be made from a bio-compatible polymer.

The hydrogel particles may swell with the liquid growth medium to form a granular gel material. Depending on the particular embodiment, the swollen hydrogel particles may have a characteristic size at the micron or submicron scales. For example, in some embodiments, the swollen hydrogel particles may have a size between about 0.1 μm and 100 μm. Furthermore, a 3D cell growth medium may have any suitable combination of mechanical properties, and in some embodiments, the mechanical properties may be tuned via the relative concentration of hydrogel particles and liquid cell growth medium. For example, a higher concentration of hydrogel particles may result in a 3D growth medium having a higher elastic modulus and/or a higher yield stress.

According to some embodiments, the 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

Regardless of how cells are placed in the medium, the yield stress of the yield stress material may be large enough to prevent yielding due to gravitational and/or diffusional forces exerted by the cells such that the position of the cells within the 3D growth medium may remain substantially constant over time. As described in more detail below, placement and/or retrieval of groups of cells may be done manually or automatically.

A yield stress material as described herein may have any suitable mechanical properties. For example, in some embodiments, a yield stress material may have an elastic modulus between approximately 1 Pa and 1000 Pa when in a solid phase or other phase in which the material retains its shape under applied stresses at levels below the yield stress. In some embodiments, the yield stress required to transform a yield stress material to a fluid-like phase may be between approximately 1 Pa and 1000 Pa. In some embodiments, the yield stress may be on the order of 10 Pa, such as 10 Pa+/−25%. When transformed to a fluid-like phase, a yield stress material may have a viscosity between approximately 1 Pa s and 10,000 Pa s. However, it should be understood that other values for the elastic modulus, yield stress, and/or viscosity of a yield stress material are also possible, as the present disclosure is not so limited.

A group of cells may be placed in a 3D growth medium made from a yield stress material via any suitable method. For example, in some embodiments, cells may be injected or otherwise placed at a particular location within the 3D growth medium with a syringe, pipette, or other suitable placement or injection device. In some embodiments an array of automated cell dispensers may be used to inject multiple cell samples into a container of 3-D growth medium. Movement of the tip of a placement device through the 3D growth medium may impart a sufficient amount of energy into a region around the tip to cause yielding such that the placement tool may be easily moved to any location within the 3D growth medium. In some instances, a pressure applied by a placement tool to deposit a group of cells within the 3D growth medium may also be sufficient to cause yielding such that the 3D growth medium flows to accommodate the group of cells. Movement of a placement tool may be performed manually (e.g. "by hand"), or may performed by a machine or any other suitable mechanism.

In some embodiments, multiple independent groups of cells may be placed within a single volume of a 3D cell growth medium. For example, a volume of 3D cell growth medium may be large enough to accommodate at least 2, at least 5, at least 10, at least 20, at least 50, at least 100, at least 1000, or any other suitable number of independent groups of cells. Alternatively, a volume of 3D cell growth medium may only have one group of cells. Furthermore, it should be understood that a group of cells may comprise any suitable number of cells, and that the cells may of one or more different types.

Depending on the particular embodiment, groups of cells may be placed within a 3D cell growth medium according to any suitable shape, geometry, and/or pattern. For example, independent groups of cells may be deposited as spheroids, and the spheroids may be arranged on a 3D grid, or any other suitable 3D pattern. The independent spheroids may all comprise approximately the same number of cells and be approximately the same size, or alternatively different spheroids may have different numbers of cells and different sizes. In some embodiments, cells may be arranged in shapes such as embryoid or organoid bodies, tubes, cylinders, toroids, hierarchically branched vessel networks, high aspect ratio objects, thin closed shells, or other complex shapes which may correspond to geometries of tissues, vessels or other biological structures.

According to some embodiments, a 3D cell growth medium made from a yield stress material may enable 3D printing of cells to form a desired pattern in three dimensions. For example, a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells. After injection, the 3D cell growth medium may transform back into a solid-like phase to support the printed cells and maintain the printed geometry. However, it should be understood that 3D printing techniques are not required to use a 3D growth medium as described herein.

According to some embodiments, a 3D cell growth medium may be prepared by dispersing hydrogel particles in a liquid cell growth medium. The hydrogel particles may be mixed with the liquid cell growth medium using a centrifugal mixer, a shaker, or any other suitable mixing device. During mixing, the hydrogel particles may swell with the liquid cell growth medium to form a material which is substantially solid when an applied shear stress is below a yield stress, as discussed above. After mixing, entrained air or gas bubbles introduced during the mixing process may be removed via centrifugation, agitation, or any other suitable method to remove bubbles from 3D cell growth medium.

In some embodiments, preparation of a 3D cell growth medium may also involve buffering to adjust the pH of a hydrogel particle and liquid cell growth medium mixture to a desired value. For example, some hydrogel particles may be made from polymers having a predominantly negative charge which may cause a cell growth medium to be overly acidic (have a pH which is below a desired value). The pH of the cell growth medium may be adjusted by adding a strong base to neutralize the acid and raise the pH to reach the desired value. Alternatively, a mixture may have a pH that is higher than a desired value; the pH of such a mixture may be lowered by adding a strong acid. According to some embodiments, the desired pH value may be in the range of about 7.0 to 7.4, or, in some embodiments 7.2 to 7.6, or any other suitable pH value which may, or may not, correspond to in vivo conditions. The pH value, for example may be approximately 7.4. In some embodiments, the pH may be adjusted once the dissolved $CO_2$ levels are adjusted to a desired value, such as approximately 5%.

Yield stress can be measured by performing a strain rate sweep in which the stress is measured at many constant strain rates. Yield stress can be determined by fitting these data to a classic Herschel-Bulkley model ($\sigma=\sigma_y+k\dot{\gamma}^n$). (b) To determine the elastic and viscous moduli of non-yielded LLS media, frequency sweeps at 1% strain can be performed. The elastic and viscous moduli remain flat and separated over a wide range of frequency, behaving like a Kelvin-Voigt linear solid with damping. Together, these rheological properties demonstrate that a smooth transition between solid and liquid phases occurs with granular microgels, facilitating their use as a 3D support matrix for cell printing, culturing, and assaying.

An example of a hydrogel with which some embodiments may operate is a carbomer polymer, such as Carbopol®. Carbomer polymers may be polyelectrolytic, and may comprise deformable microgel particles. Carbomer polymers are particulate, high-molecular-weight crosslinked polymers of acrylic acid with molecular weights of up to 3-4 billion Daltons. Carbomer polymers may also comprise co-polymers of acrylic acid and other aqueous monomers and polymers such as poly-ethylene-glycol.

While acrylic acid is a common primary monomer used to form polyacrylic acid the term is not limited thereto but includes generally all α-β unsaturated monomers with carboxylic pendant groups or anhydrides of dicarboxylic acids and processing aids as described in U.S. Pat. No. 5,349,030. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2, 340, 111; and 2,533,635. The disclosures of all of these U.S. Patents are hereby incorporated herein by reference for their discussion of carboxylic polymers and copolymers that, when used in polyacrylic acids, form yield stress materials as otherwise disclosed herein.

Specific types of cross-linked polyacrylic acids include carbomer homopolymer, carbomer copolymer and carbomer interpolymer monographs in the U.S. Pharmocopia 23 NR 18, and Carbomer and C10-30 alkylacrylate crosspolymer, acrylates crosspolymers as described in PCPC International Cosmetic Ingredient Dictionary & Handbook, 12th Edition (2008).

Carbomer polymer dispersions are acidic with a pH of approximately 3. When neutralized to a pH of 6-10, the particles swell dramatically. The addition of salts to swelled Carbomer can reduce the particle size and strongly influence their rheological properties. Swelled Carbomers are nearly refractive index matched to solvents like water and ethanol, making them optically clear. The original synthetic powdered Carbomer was trademarked as Carbopol® and commercialized in 1958 by BF Goodrich (now known as Lubrizol), though Carbomers are commercially available in a multitude of different formulations.

In some embodiments, the hydrogels are non-Carbomer microgels made from one or more of polyethylene glycol, polyacrylamide, or polyacrylic acid.

Hydrogels may include packed microgels—microscopic gel particles, ~5 µm in diameter, made from crosslinked polymer. The yield stress of the packed microgels can controlled by water content. Packed microgel yield stress can be varied between roughly 1-1000 Pa. Thus, both materials can be tuned to span the stress levels that cells typically generate. As discussed above, while materials may have yield stresses in a range of 1-1000 Pa, in some embodiments it may be advantageous to use yield stress materials having yield stresses in a range of 1-100 Pa or 10-100 Pa. In addition, some such materials may have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

Liquid Medium

Liquid medium composition must be considered from two perspectives: basic nutrients (sugars, amino acids) and growth factors/cytokines. Co-culture of cells often allows reduction or elimination of serum from the medium due to production of regulatory macromolecules by the cells themselves. The ability to supply such macromolecular regulatory factors in a physiological way is a primary reason 3D perfused co-cultures are used. A serum-free medium supplemented with several growth factors suitable for long-term culture of primary differentiated hepatocytes has been tested and found to support co-culture of hepatocytes with endothelial cells. ES cells are routinely maintained in a totipotent state in the presence of leukemia inhibitory factor (LIF), which activates gp130 signaling pathways. Several medium formulations can support differentiation of ES cells, with different cytokine mixes producing distinct patterns of differentiation. Medium replacement rates can be determined by measuring rates of depletion of key sugars and amino acids as well as key growth factors/cytokines. If cell culture medium with sodium bicarbonate is used, the environmental control can be provided by e.g. placing the module with bioreactor/reservoir pairs into a $CO_2$ incubator.

Cells

A variety of different cells can be applied to the 3D growth medium of the disclosed systems. In the some embodiments, these are normal human cells or human tumor cells. The cells may be a homogeneous suspension or a mixture of cell types. The different cell types may be seeded onto and/or into the medium sequentially, together, or after an initial suspension is allowed to attach and proliferate (for example, endothelial cells, followed by liver cells). Cells can be obtained from cell culture or biopsy. Cells can be of one or more types, either differentiated cells, such as endothelial cells or parenchymal cells, including nerve cells, or undifferentiated cells, such as stem cells or embryonic cells. In one embodiment, the medium is seeded with a mixture of cells including endothelial cells, or with totipotent/pluripotent stem cells which can differentiate into cells including endothelial cells, which will form "blood vessels", and at least one type of parenchymal cells, such as hepatocytes, pancreatic cells, or other organ cells.

Cells can be cultured initially and then used for screening of compounds for toxicity. Cells can also be used for screening of compounds having a desired effect. For example endothelial cells can be used to screen compounds which inhibit angiogenesis. Tumor cells can be used to screen compounds for anti-tumor activity. Cells expressing certain ligands or receptors can be used to screen for compounds binding to the ligands or activating the receptors. Stem cells can be seeded, alone or with other types of cells. Cells can be seeded initially, then a second set of cells introduced after the initial bioreactor tissue is established, for example, tumor cells that grow in the environment of liver tissue. The tumor cells can be studied for tumor cell behaviors or molecular events can be visualized during tumor cell growth. Cells can be modified prior to or subsequent to introduction into the apparatus. Cells can be primary tumor cells from patients for diagnostic and prognostic testing. The tumor cells can be assessed for sensitivity to an agent or gene therapy. Tumor cell sensitivity to an agent or gene therapy can be linked to liver metabolism of set agent or gene therapy. Cells can be stem or progenitor cells and the stem or progenitor cells be induced to differentiate by the mature tissue. Mature cells can be induced to replicate by manipulation of the flow rates or medium components in the system.

System

Turning now to the figures, specific non-limiting embodiments of bioreactor system are described in more detail.

Figure 1:
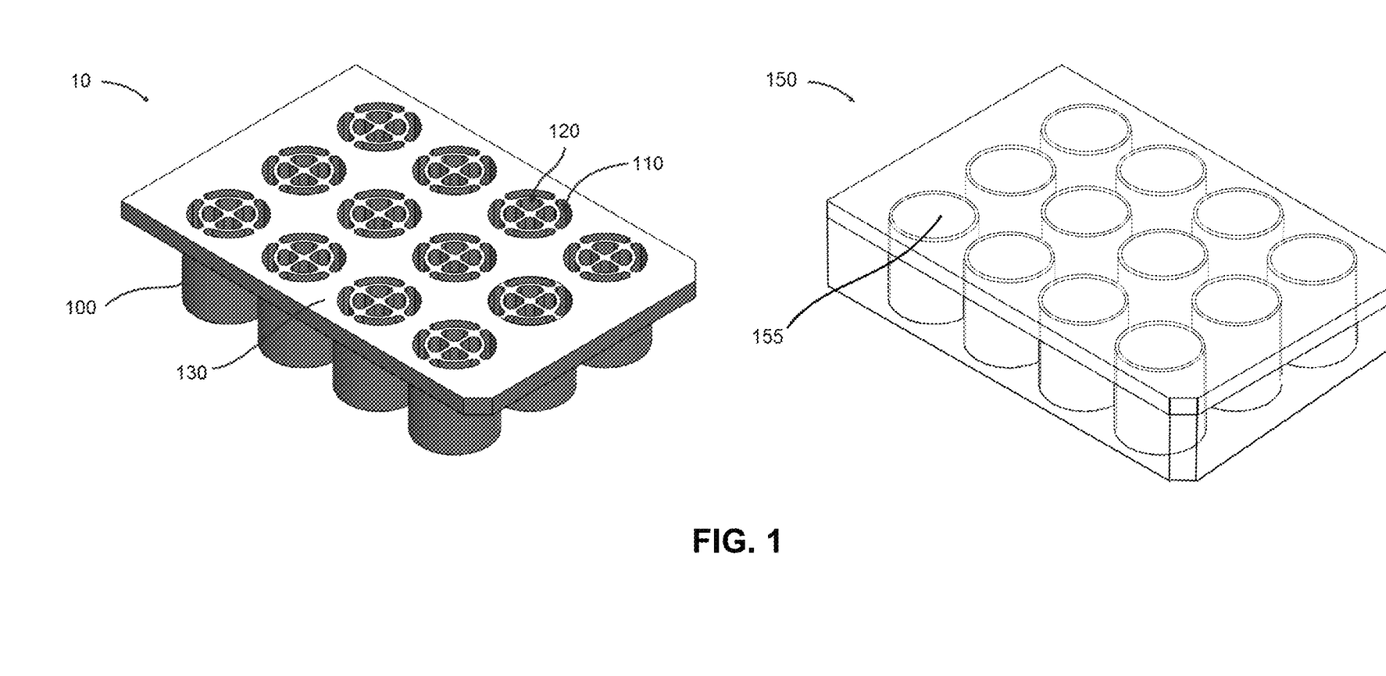
FIG. 1 is a perspective view of an embodiment of a disclosed bioreactor system that includes a plurality of cylindrical well-plate inserts and a well-plate containing a plurality of wells.
Figure 2:
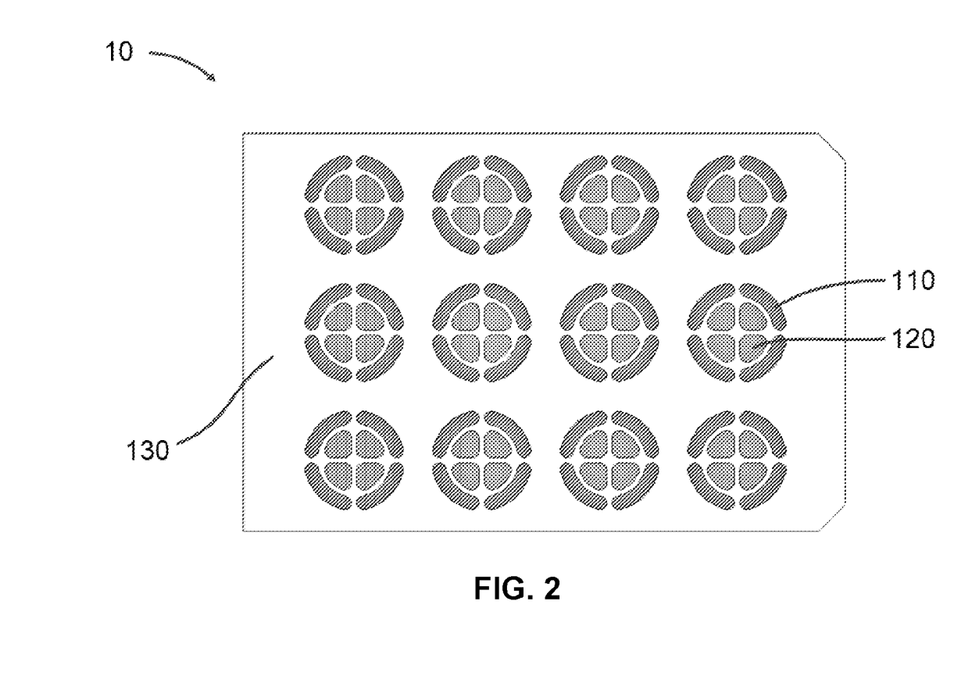
FIG. 2 is a top view of an embodiment of a disclosed bioreactor system.
Figure 3:
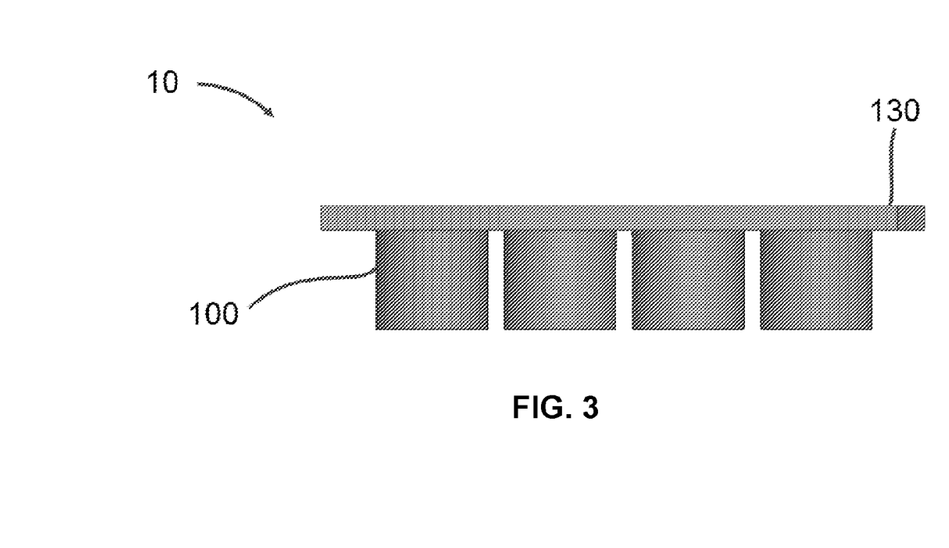
FIG. 3 is a side view of an embodiment of a disclosed bioreactor system.
Figure 4:
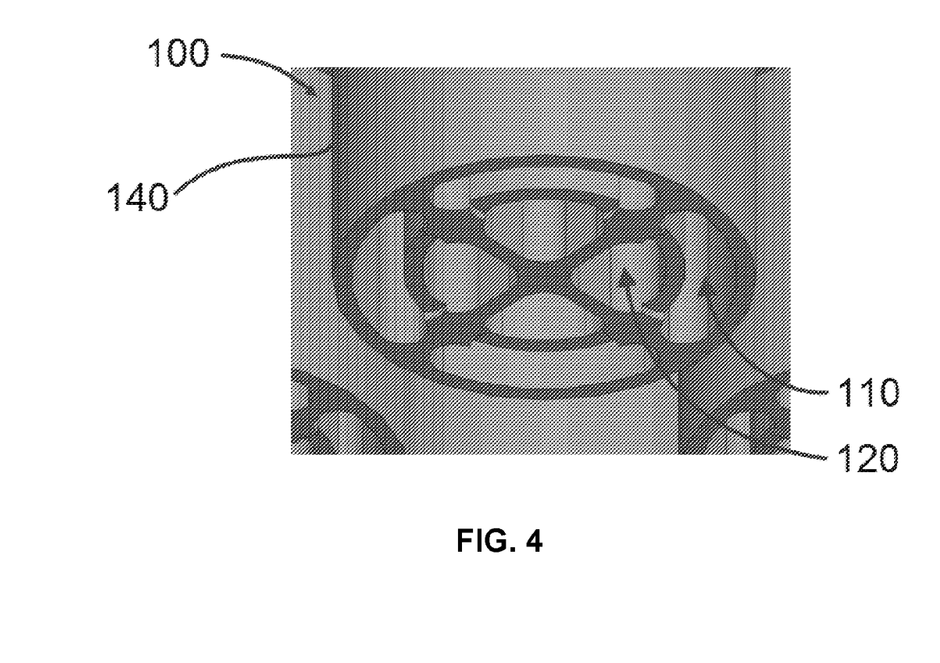
FIG. 4 is a perspective view of an embodiment of a well-plate insert in an embodiment of the disclosed bioreactor system.

As shown in FIG. 1 a bioreactor system 10 is disclosed that includes a plurality of cylindrical well-plate inserts 100 that can be positioned inside wells 155 of a well-plate 150. Each insert 100 is divided into at least one printing well 110 and at least one collection chamber 120 each extending from the top opening and in fluid communication with the well of the well plate.

Figure 5:
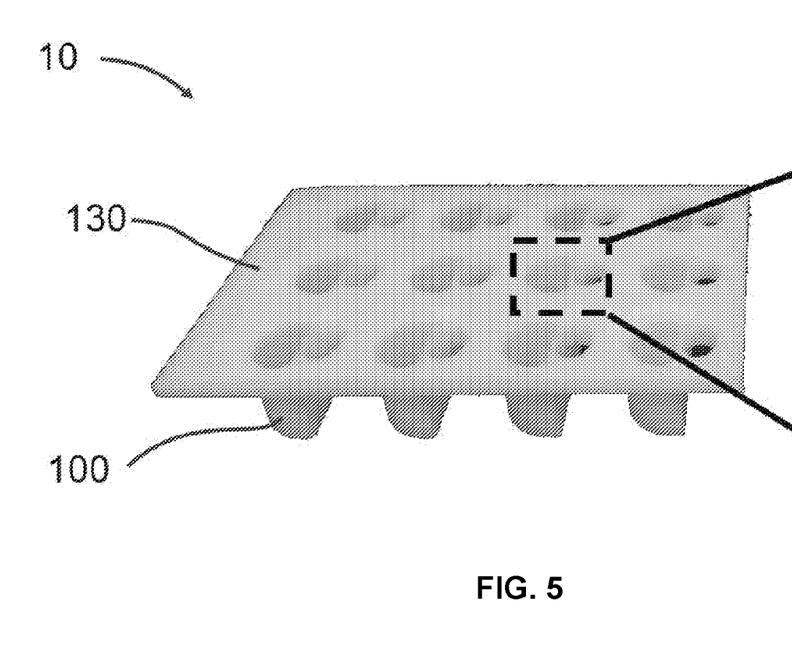
FIG. 5 is a top perspective view of an embodiment of a disclosed bioreactor system.
Figure 6:
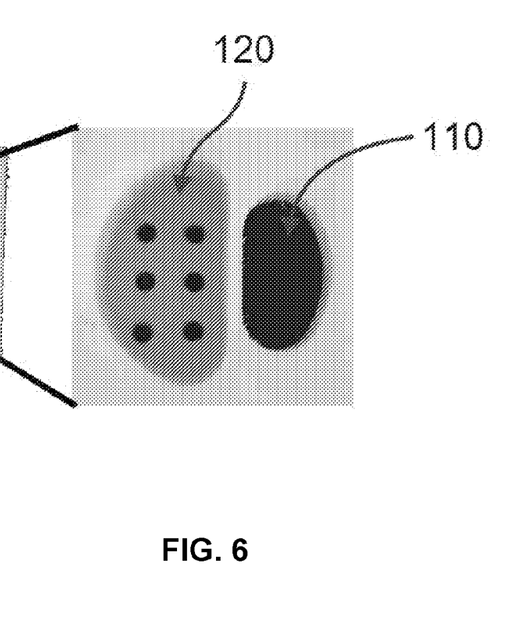
FIG. 6 is a top view of an embodiment of a well in an embodiment of the disclosed bioreactor system.
Figure 7:
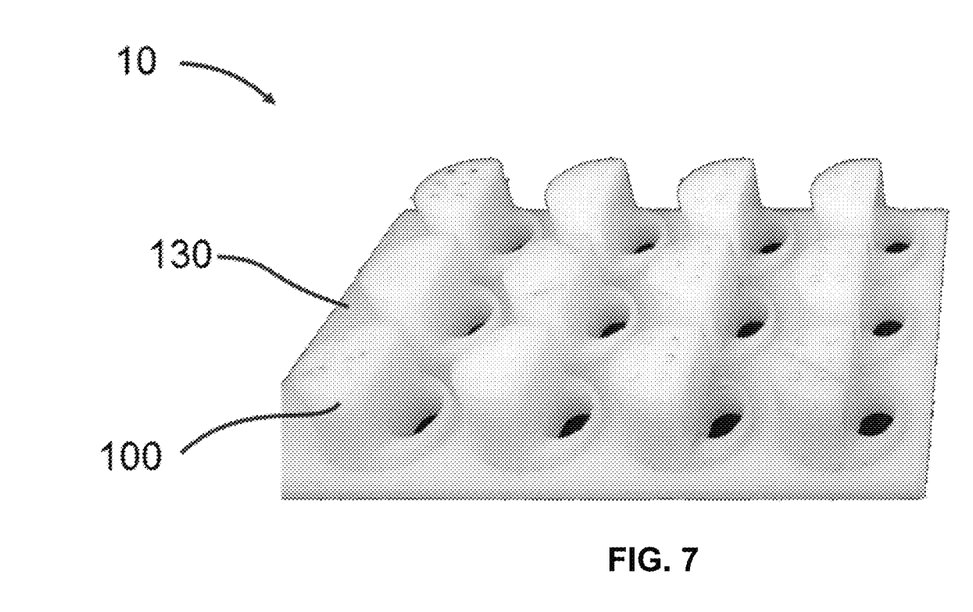
FIG. 7 is a bottom perspective view of an embodiment of a disclosed bioreactor system.
Figure 8:
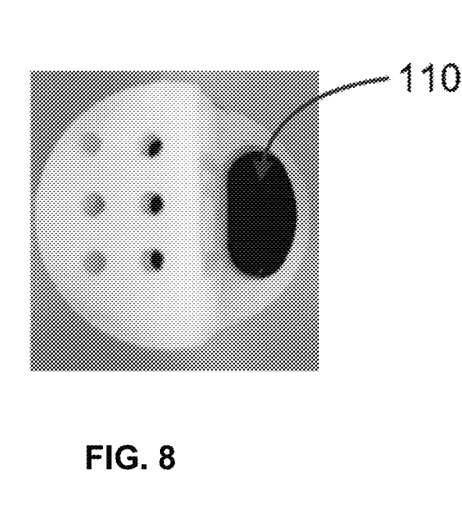
FIG. 8 is a bottom view of an embodiment of a well in an embodiment of the disclosed bioreactor system.

As shown in FIG. 1, each insert 100 can have a plurality of printing wells 110 and collection chambers 120. The inserts 100 of FIG. 1 each have four printing wells 110 and four collection chambers 120. In contrast, the inserts 100 of FIG. 5 each have one printing well 110 and one collection chamber 120. In addition, the printing wells 110 and collection chambers 120 can be configured within the inserts 100 in any orientation. For example, in FIG. 1, the collection chambers 120 are positioned radially from the printing wells 110, wherein is FIG. 5, the collection chambers 120 is positioned adjacent to the printing well 110. In some embodiments, the printing well(s) 110 are positioned radially from the collection chamber(s) 120. Suitable configurations are generally determined by volume requirements.

Each insert can have a top opening, a bottom opening, and a cylindrical wall 140. In some embodiments, the plurality of cylindrical well-plate inserts 100 are connected by a planar surface 130 with a plurality of holes that define the top openings for each printing well 110 and collection chamber 120.

Figure 9:
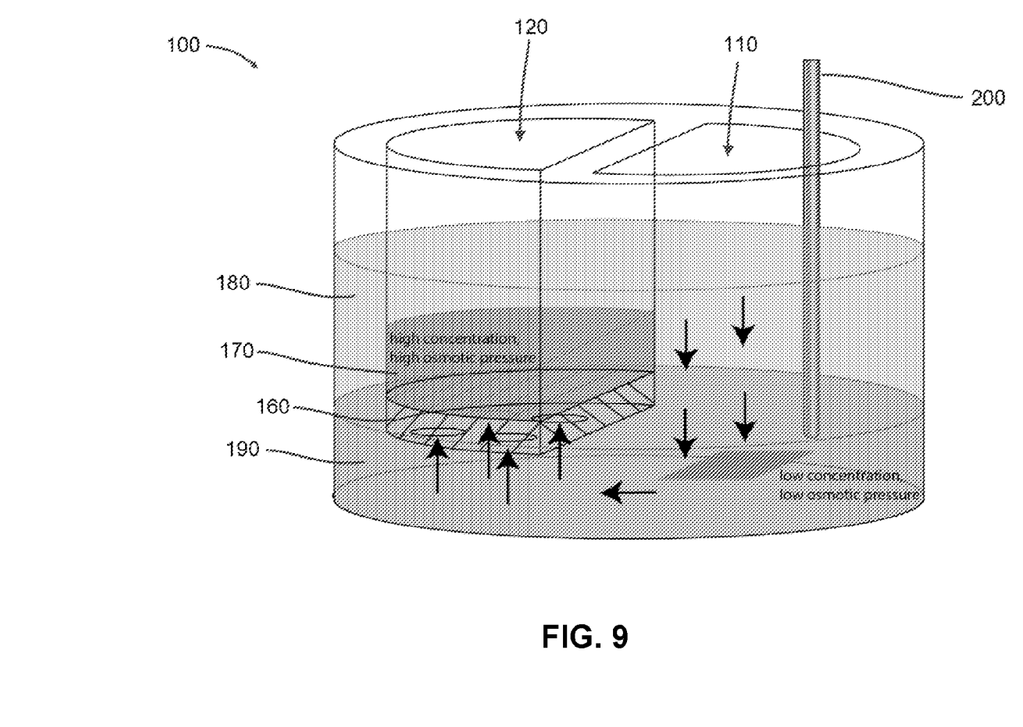
FIG. 9 is a perspective view of an embodiment of a well in an embodiment of the disclosed bioreactor system
Figure 10A:
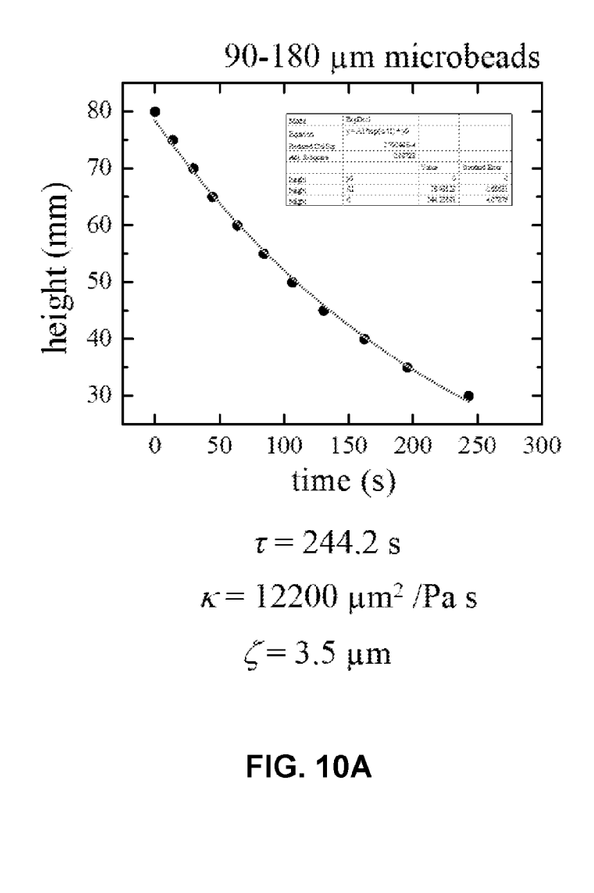
FIGS. 10A and 10B are graphs showing gravity-driven perfusion through charge neutral polyacrylamide 90-180 μm (FIG. 10A) and <45 μm (FIG. 10B) microbeads (height (mm) as a function of time (s)).
Figure 10B:
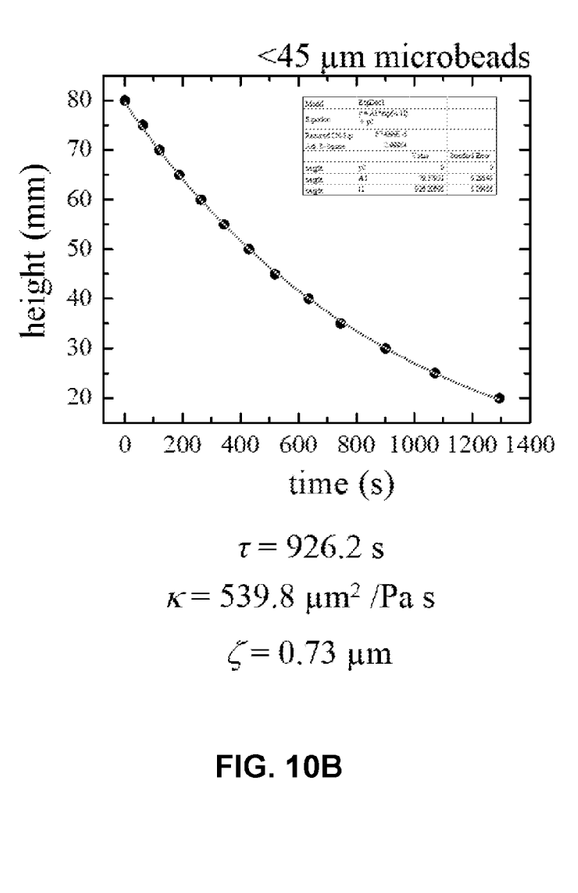
Figure 11:
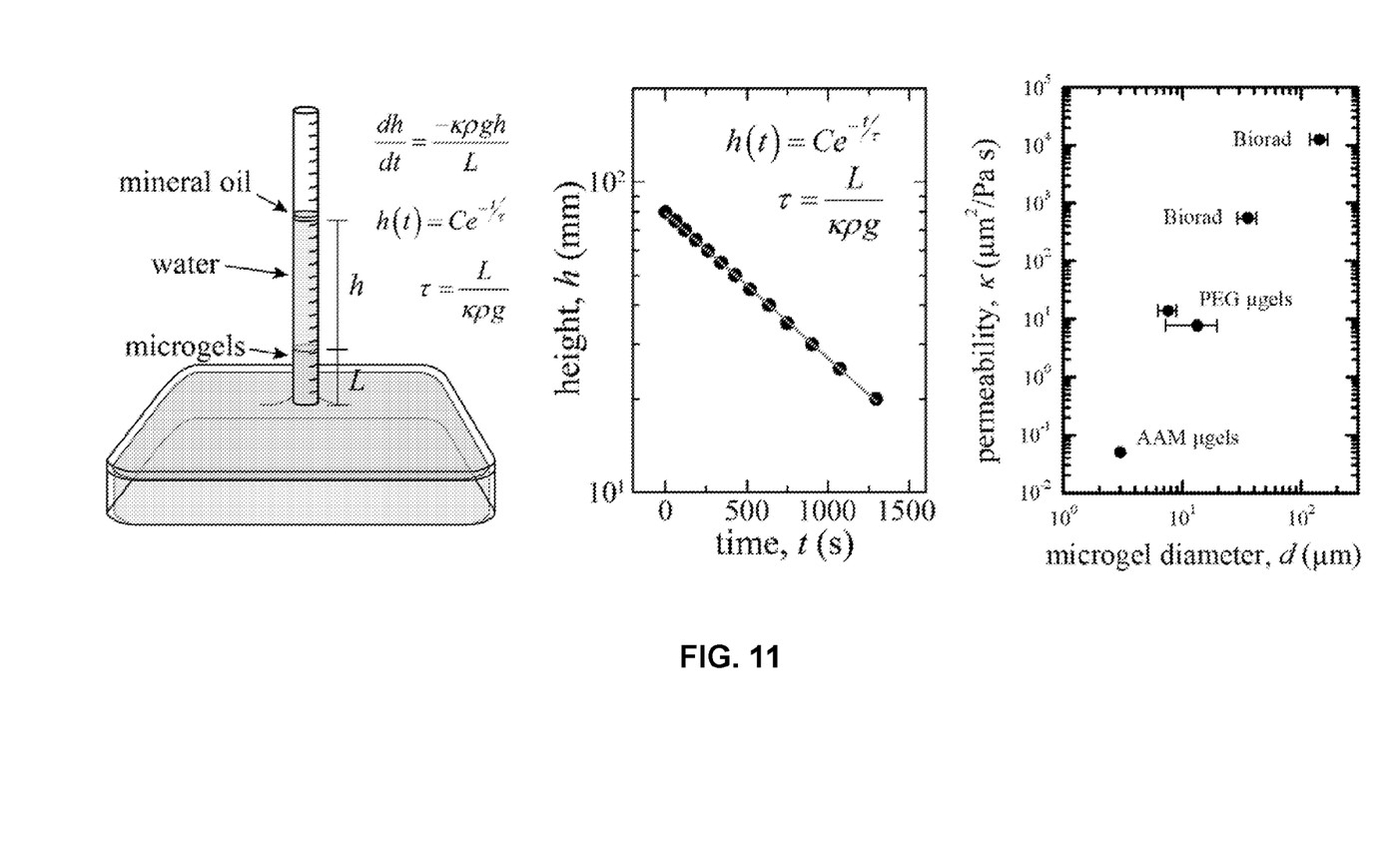
FIG. 11 shows perfusion through microgels and permeability measurements for several different microgel systems.
Figure 12:
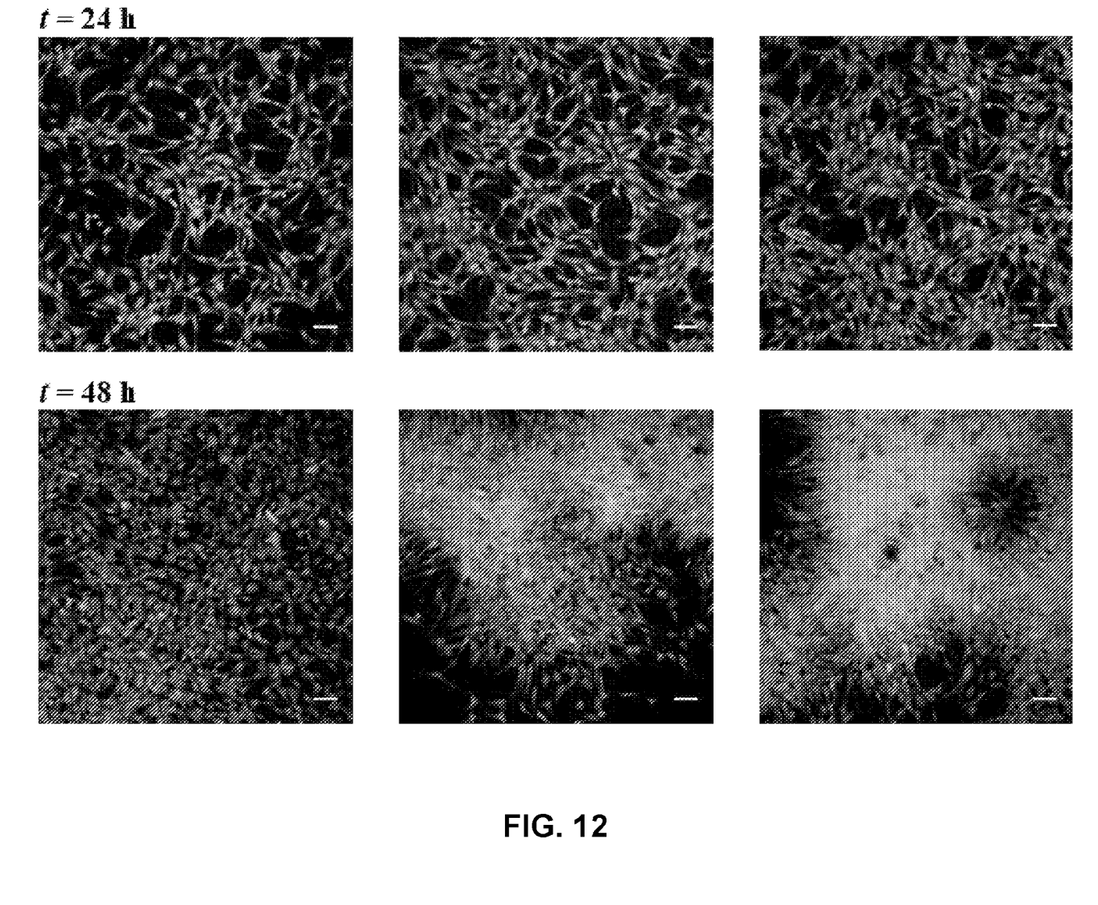
FIG. 12 shows 3T3 cells cultured with microgel media on top. 4.5 wt % PEG microgels were used. The images show live and dead cells after 24 hours (top) and 48 hours (bottom), demonstrating 98% viability after 24 hours. Scale bar: 100 μm.

As shown in FIG. 9, the well plate can be filled with a three-dimensional (3D) cell growth medium 190 that comprises a plurality of hydrogel particles and a liquid cell culture medium, wherein the hydrogel particles are swelled with the liquid cell culture medium to form a granular gel.

In addition, the printing well is preferably configured to provide an injection needle 200 unencumbered access to the 3D cell growth medium for 3D printing.

The collection chamber 120 can be filled with an absorbant material 170 that is separated from the well of the well-plate by a filter material 160. In these embodiments, the absorbant material 170 establishes an osmotic pressure gradient that draws fluid 180 from the well of the well plate where it permeates the 3D cell growth medium 190, through the filter material 160, and finally into the absorbant material 170 of the collection chamber 120. In preferred embodiments, the filter material 160 has a porosity smaller than the size of the swollen hydrogel particles.

In some embodiments, the disclosed sample wells can be used for culturing cells (such as tumor samples) in a 3D cell growth medium, which allows the nutrient media to perfuse through the system without disturbing the cellular environment. The wells of the bioreactor system are preferably arrayed in columns and rows. The depicted bioreactor system uses an osmotic gradient to draw media from the sample wells through a filter material and into a media collection chamber. For example, an osmotic gradient can be generated, for example, by placing an absorbant material in the collection chamber.

In some embodiments of the bioreactor system, medium flows with gravity. In some embodiments of the bioreactor system, medium flows radially outward or radially inward.

As described above, the 3D cell growth medium for each of the above depicted systems may include a thixotropic or yield stress material, or any material suitable for temporary phase changing. In some examples, the thixotropic or yield stress material may include a soft granular gel. The soft granular gel may be made from polymeric hydrogel particles swelled with a liquid cell culture medium. Depending on the particular embodiment, the hydrogel particles may be between 0.5 µm and 50 µm in diameter, between about 1 µm and 10 µm in diameter, or about 5 µm in diameter when swelled.

Sensors can be used to detect changes in pH, oxygen levels, specific metabolites such as glucose, presence or absence of an indicator molecule such as a viral protein, or any other indicia of an effect on the tissues or a material exposed to the tissues within the bioreactor.

Applications

The system has many different applications, such as identification of markers of disease; assessing efficacy of anti-cancer therapeutics; testing gene therapy vectors; drug development; screening; studies of cells, especially stem cells; studies on biotransformation, clearance, metabolism, and activation of xenobiotics; studies on bioavailability and transport of chemical agents across epithelial layers; studies on bioavailability and transport of biological agents across epithelial layers; studies on transport of biological or chemical agents across the blood-brain barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratinogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical agents to treat disease; studies on the efficacy of biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; filter or porous material below microscale tissue may be chosen or constructed so as bind denatured, single-stranded DNA; studies on gene transcription in response to chemical or biological agents; studies on protein expression in response to chemical or biological agents; studies on changes in metabolism in response to chemical or biological agents; prediction of agent impact through database systems and associated models; prediction of agent impact through expert systems; and prediction of agent impact through structure-based models.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A bioreactor system, comprising a plurality of cylindrical well-plate inserts positioned inside wells of a well-plate, each insert having a top opening, a bottom opening, and a cylindrical wall,
   wherein each insert is divided into at least one printing well and at least one collection chamber,
   wherein the printing well is filled with a three-dimensional (3D) cell growth medium that comprises a plurality of hydrogel particles and a liquid cell culture medium, wherein the hydrogel particles are swelled with the liquid cell culture medium to form a granular gel,
   wherein the printing well is configured to provide unencumbered access to the 3D cell growth medium for 3D printing,
   wherein the collection chamber is filled with an absorbant material that is separated from the well of the well-plate by a filter material,
   wherein the absorbant material establishes an osmotic pressure gradient that draws the liquid cell culture medium from the well of the well-plate where the liquid cell culture medium permeates the 3D cell growth medium, through the filter material, and finally into the absorbant material of the collection chamber, and
   wherein the filter material has a porosity smaller than the size of the swollen hydrogel particles.

2. The bioreactor system of claim 1, wherein the plurality of cylindrical well-plate inserts are connected by a planar surface with a plurality of holes that define the top openings of the inserts.

3. The system of claim 1, wherein the bottom of the sample well is optically transparent.

4. The system of claim 1, wherein the three-dimensional cell growth medium has a yield stress such that the cell growth medium undergoes a phase change from a first solid phase to a second liquid phase upon application of a shear stress greater than the yield stress.

5. The system of claim 4, wherein the yield stress is on the order of 10 Pa.

6. The system of claim 1, wherein the concentration of the hydrogel particles in the three-dimensional (3D) cell growth medium is between 0.05% to about 1.0% by weight.

7. The system of claim 1, wherein the hydrogel particles have a size between about 0.1 μm to about 100 μm when swollen with the liquid cell culture medium.

8. The system of claim 1, wherein a plurality of cells are disposed in a region of the 3D cell culture medium.

* * * * *